United States Patent
Matsuda

(10) Patent No.: US 8,478,010 B2
(45) Date of Patent: Jul. 2, 2013

(54) IMAGE PROCESSING APPARATUS, IMAGE PROCESSING PROGRAM RECORDING MEDIUM, AND IMAGE PROCESSING METHOD

(75) Inventor: Takehiro Matsuda, Hachioji (JP)

(73) Assignee: Olympus Corporation, Tokyo (JP)

( * ) Notice: Subject to any disclaimer, the term of this patent is extended or adjusted under 35 U.S.C. 154(b) by 283 days.

(21) Appl. No.: 12/971,500

(22) Filed: Dec. 17, 2010

(65) Prior Publication Data

US 2011/0085717 A1    Apr. 14, 2011

Related U.S. Application Data

(63) Continuation of application No. PCT/JP2009/060643, filed on Jun. 10, 2009.

(30) Foreign Application Priority Data

Jun. 17, 2008  (JP) ................. 2008-158389

(51) Int. Cl.
 *G06K 9/00*   (2006.01)
(52) U.S. Cl.
 USPC ...................................... 382/128
(58) Field of Classification Search
 USPC ...................................... 382/128
 See application file for complete search history.

(56) References Cited

U.S. PATENT DOCUMENTS

| 7,200,253 | B2 * | 4/2007 | Glukhovsky et al. | 382/128 |
| 7,553,276 | B2 * | 6/2009 | Iddan | 600/160 |
| 7,634,305 | B2 * | 12/2009 | Davidson et al. | 600/424 |
| 8,175,347 | B2 * | 5/2012 | Hirakawa | 382/128 |

FOREIGN PATENT DOCUMENTS

| JP | 2002-099896 | 4/2002 |
| JP | 2002-257534 | 9/2002 |
| JP | 2005-192880 | 7/2005 |

OTHER PUBLICATIONS

International Search Report dated Jul. 21, 2009.

* cited by examiner

*Primary Examiner* — Tom Y Lu
(74) *Attorney, Agent, or Firm* — Scully, Scott, Murphy & Presser, P.C.

(57) ABSTRACT

An image processing apparatus includes: a model estimator that models gradient variations of pixel values in an image of a captured object, which is an in-vivo image, according to the pixel values in the image; and an abnormality candidate detector that detects an abnormality candidate area on the object shown in the image according to a difference between a pixel value of each pixel constituting the image and an estimated pixel value of each pixel, the estimated pixel value being determined according to the modeled gradient variations of the pixel values.

23 Claims, 18 Drawing Sheets

INITIAL UPLIFT MODEL

IMAGE PROCESSING APPARATUS, IMAGE PROCESSING PROGRAM RECORDING MEDIUM, AND IMAGE PROCESSING METHOD

CROSS-REFERENCE TO RELATED APPLICATIONS

This application is a continuation of PCT international application Ser. No. PCT/JP2009/060643 filed on Jun. 10, 2009 which designates the United States, incorporated herein by reference, and which claims the benefit of priority from Japanese Patent Application No. 2008-158389, filed on Jun. 17, 2008, incorporated herein by reference.

BACKGROUND OF THE INVENTION

1. Field of the Invention

The present invention relates to an image processing apparatus that processes an image of a captured object, an image processing program recording medium, and an image processing method.

2. Description of the Related Art

In recent years, medical image processing apparatuses, as represented by capsule endoscopes, that sequentially capture time-series in-vivo images of a lumen while moving through the lumen have been developed. When a capsule endoscope is swallowed by a patient and thus introduced into the body, the capsule endoscope sequentially captures images and transmits the images to a receiving device outside the body while moving through the lumen due to peristalsis. The capsule endoscope is eventually excreted to the outside of the body. The in-vivo images of the subject that are captured by the capsule endoscope and then received by the external receiving device are sequentially displayed in chronological order on, for example, a diagnostic workstation and are checked by an observer, such as a doctor.

The capsule endoscope captures a large number of images. The diagnostic workstation performs a process for detecting, from the captured images, images from which possible abnormalities, such as bleeding, can be assumed as images to be observed, which reduces the burden of observing images on a doctor and the like. For example, a technique is well known in which an image is divided into blocks, tone information is calculated per block, the calculated tone information is clustered, and a block, which belongs to a cluster at a predetermined distance from a cluster of blocks constituting a normal mucosa, is extracted as an abnormal site (Japanese Laid-open Patent Publication No. 2005-192880). A technique is also well known in which an image with highlighted microcalcification shades is generated using a morphology filter that is a shape-dependent filter for detecting candidates of microcalcification shades (Japanese Laid-open Patent Publication No. 2002-99896).

SUMMARY OF THE INVENTION

An image processing apparatus according to an aspect of the present invention includes: a model estimator that models gradient variations of pixel values in an image of a captured object, which is an in-vivo image, according to the pixel values in the image; and an abnormality candidate detector that detects an abnormality candidate area on the object shown in the image according to a difference between a pixel value of each pixel constituting the image and an estimated pixel value of each pixel, the estimated pixel value being determined according to the modeled gradient variations of the pixel values.

An image processing program recording medium according to another aspect of the present invention stores thereon instructions that causes a computer to perform: a model estimating procedure that models gradient variations of pixel values in an image of a captured object, which is an in-vivo image, according to the pixel values in the image; and an abnormality candidate detecting procedure that detects an abnormality candidate area on the object shown in the image according to a difference between a pixel value of each pixel constituting the image and an estimated pixel value of each pixel, the estimated pixel value being determined according to the modeled gradient variations of the pixel values.

An image processing method according to still another aspect of the present invention includes: a model estimating step that models gradient variations of pixel values in an image of a captured object, which is an in-vivo image, according to the pixel values in the image; and an abnormality candidate detecting step that detects an abnormality candidate area on the object shown in the image according to a difference between a pixel value of each pixel constituting the image and an estimated pixel value of each pixel, the estimated pixel value being determined according to the modeled gradient variations of the pixel values.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
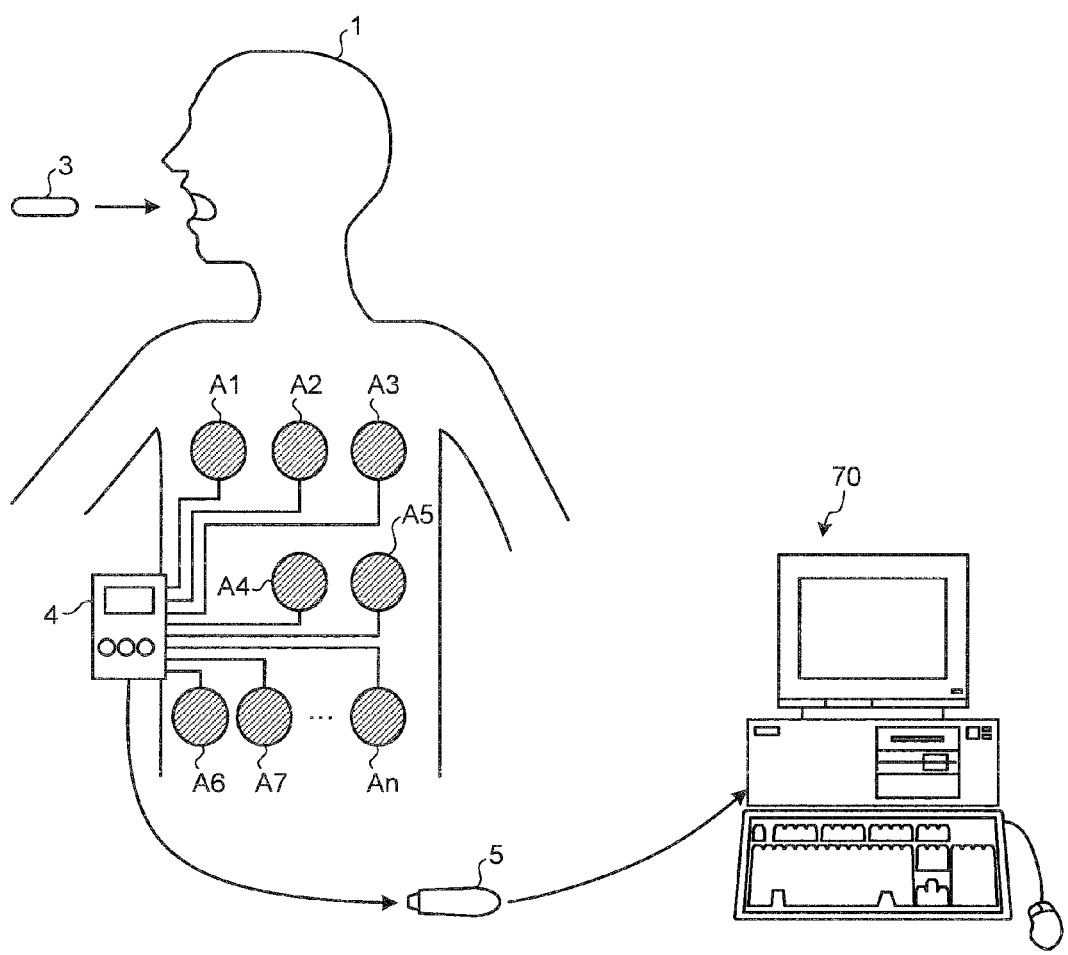
FIG. 1 is a schematic diagram illustrating an entire configuration of an image processing system that includes an image processing apparatus.

Exemplary embodiments of the present invention will be described in detail below with reference to the drawings. Hereinafter, an image processing apparatus that uses a capsule endoscope, which moves through a lumen in a body, will be described. The image processing apparatus processes images that are captured sequentially by the capsule endoscope while the capsule endoscope moves through the lumen in the body. The embodiments do not limit the present invention. In the drawings, like reference numerals/symbols designate like parts.

FIG. 1 is a schematic diagram illustrating an entire configuration of an image processing system that includes an image processing apparatus 70 according to an embodiment. As illustrated in FIG. 1, the image processing system includes a capsule endoscope 3 that captures in-vivo images in a lumen of a subject 1 (hereinafter "lumen in-vivo images"); a receiving device 4 that receives image data of lumen in-vivo images that are transmitted by radio from the capsule endoscope 3; and the image processing apparatus 70 that processes the lumen in-vivo images that are received by the receiving device 4. For example, a recording medium 5 that is portable (portable recording medium) is used for transmission and reception of image data between the receiving device 4 and the image processing apparatus 70.

The capsule endoscope 3 has an imaging function, a radio function, and an illumination function for illuminating a site to be imaged. The capsule endoscope 3 is swallowed by the subject 1, such as a human or an animal, and is introduced into the subject 1 for e.g. examination. Until the capsule endoscope 3 is naturally excreted, the capsule endoscope 3 sequentially captures and acquires lumen in-vivo images of, for example, the esophagus, the stomach, the small intestine, and the large intestine at a predetermined imaging rate and transmits the lumen in-vivo images by radio to the outside of the body.

The receiving device 4 includes receiving antennas A1 to An that are discretely arranged in positions on the body surface, which correspond to the path in which the capsule endoscope 3 passes through in the subject 1. The receiving device 4 receives image data that is transmitted by radio from the capsule endoscope 3 via the receiving antennas A1 to An. The receiving device 4 is configured such that the portable recording medium 5 can be attached and detached, and the receiving device 4 saves the received image data in the portable recording medium 5 each time image data is received. Thus, the receiving device 4 stores lumen in-vivo images of the subject 1, which are captured by the capsule endoscope 3, in the portable recording medium 5 in chronological order.

The image processing apparatus 70 is realized using a general-purpose computer, such as a work station or a personal computer. The image processing apparatus 70 is configured such that the portable recording medium 5 can be attached and detached. The image processing apparatus 70 acquires lumen in-vivo images that are saved in the portable recording medium 5, processes the lumen-in-vivo images, and displays the processed lumen-in-vivo images on the screen of a display device.

Figure 2:
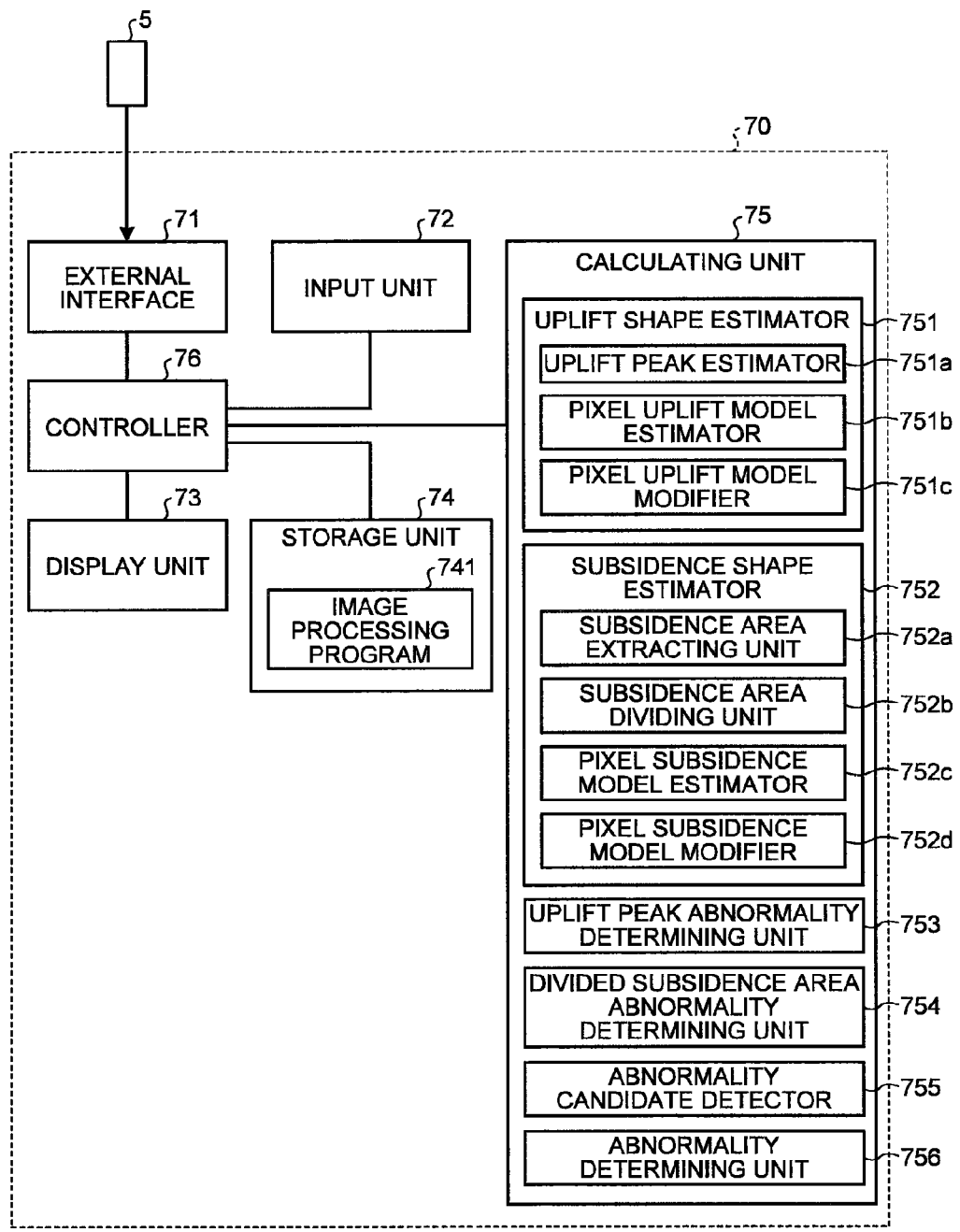
FIG. 2 is a block diagram illustrating a functional configuration of the image processing apparatus.

FIG. 2 is a block diagram illustrating a functional configuration of the image processing apparatus 70. In this embodiment, the image processing apparatus 70 includes an external interface 71, an input unit 72, a display unit 73, a storage unit 74, a calculating unit 75, and a controller 76 that controls all the operations of the image processing apparatus 70.

The external interface 71 captures image data of the lumen in-vivo images that are captured by the capsule endoscope 3 and then received by the receiving device 4. The external interface 71 may be, for example, a reader device to and from which the portable recording medium 5 is attached and detached to read the image data of the lumen in-vivo images that are saved in the portable recording medium 5. Acquisition of time-series lumen in-vivo images that are captured by the capsule endoscope 3 are not limited to the configuration using the portable recording medium 5. For example, a configuration may be employed in which, instead of the portable recording medium 5, an additional server may be arranged to save time-series lumen in-vivo images beforehand. In such a case, the external interface is configured as a communication device for establishing connection with the server. Via the external interface, data communications with the server are established to acquire time-series lumen in-vivo images. Alternatively, a configuration may be employed in which time-series lumen in-vivo images captured by the capsule endoscope 3 are saved beforehand in the storage unit 74.

The input unit 72 is realized by, for example, a keyboard, a mouse, a touch panel, and various switches. The input unit 72 outputs input instruction information to the controller 76. The display unit 73 is realized using a display device, such as an LCD, an EL display, or a CRT display. Under control of the controller 76, the display unit 73 displays various screens including the screen on which time-series lumen in-vivo images are displayed.

The storage unit 74 is realized using various IC memories, such as rewritable flash memories, including a ROM and a RAM; a hard disk that is incorporated or connected via a data communication terminal; an information recording medium, such as a CD-ROM; and a reading device for the information recording medium. The storage unit 74 stores programs for operating the image processing apparatus 70 and performing various functions of the image processing apparatus 70 and stores data that are used during execution of the programs. The storage unit 74 also stores an image processing program 741 for the calculating unit 75 to detect an abnormal site that is shown in a lumen in-vivo image.

The calculating unit 75 performs various calculation processes for processing a lumen in-vivo image that is captured by the capsule endoscope 3 and for detecting an abnormal site that is shown in the lumen in-vivo image. The calculating unit 75 includes an uplift shape estimator 751 and a subsidence shape estimator 752 that serve as model estimators, an uplift peak abnormality determining unit 753, a divided subsidence area abnormality determining unit 754 that serves as a subsidence area abnormality determining unit, an abnormality candidate detector 755, and an abnormality determining unit 756.

The uplift shape estimator 751 estimates an uplift shape that is shown in a lumen in-vivo image. The uplift shape estimator 751 includes an uplift peak estimator 751a, a pixel uplift model estimator 751b that serves as an initial uplift gradient model setting unit, and a pixel uplift model modifier 751c that serves as an uplift gradient model modifier. The uplift peak estimator 751a detects a peak area of an uplift area that shows an uplift shape (hereinafter "uplift peak area") and estimates the uplift peak area as an approximate position of the uplift area. The pixel uplift model estimator 751b generates an initial uplift model (initial uplift gradient model), which is an initial state of a pixel uplift model (uplift gradient model) that is obtained by modeling gradient variations in pixel values of the uplift peak area. The pixel uplift model modifier 751c modifies the initial uplift model according to the pixel values of the uplift area and sets a pixel uplift model in the uplift area.

The subsidence shape estimator 752 estimates a subsidence shape that is shown in a lumen in-vivo image. The subsidence shape estimator 752 includes a subsidence area extracting unit 752a, a subsidence area dividing unit 752b, a pixel subsidence model estimator 752c that serves as an initial subsidence gradient model setting unit, and a pixel subsidence model modifier 752d that serves as a subsidence gradient model modifier. The subsidence area extracting unit 752a extracts, as a subsidence area, an area in the image excluding the uplift areas. The subsidence area dividing unit 752b divides the subsidence area according to the positions of proximate uplift areas. The pixel subsidence model estimator 752c generates an initial subsidence model (initial subsidence gradient model), which is an initial state of a pixel subsidence model (subsidence gradient model) that is obtained by modeling gradient variations in pixel values of the subsidence areas that are divided (hereinafter "divided subsidence areas"). The pixel subsidence model modifier 752d modifies the initial subsidence model according to the pixel values of the divided subsidence area and sets a pixel subsidence model in the divided subsidence area.

The uplift peak abnormality determining unit 753 determines whether an uplift peak area is an abnormality candidate area according to feature data of the uplift peak area. The divided subsidence area abnormality determining unit 754 determines whether the divided subsidence area is an abnormality candidate area according to feature data of the divided subsidence area. The abnormality candidate detector 755 detects, as pixels constituting an abnormality candidate area, pixels deviating from the pixel uplift model in the uplift area. The abnormality candidate detector 755 also detects, as pixels constituting an abnormality candidate area, pixels deviating from the pixel subsidence model in the divided subsidence area. The abnormality determining unit 756 determines whether an abnormality candidate area is an abnormal site according to feature data of the abnormality candidate area.

The controller 76 is realized using hardware, such as a CPU. The controller 76 controls the whole operations of the image processing apparatus 70 by transferring instructions and data to each unit forming the image processing apparatus 70 in accordance with image data, which is acquired via the external interface 71, operation signals, which are input from the input unit 72, and the programs and data, which are stored in the storage unit 74.

Figure 3:
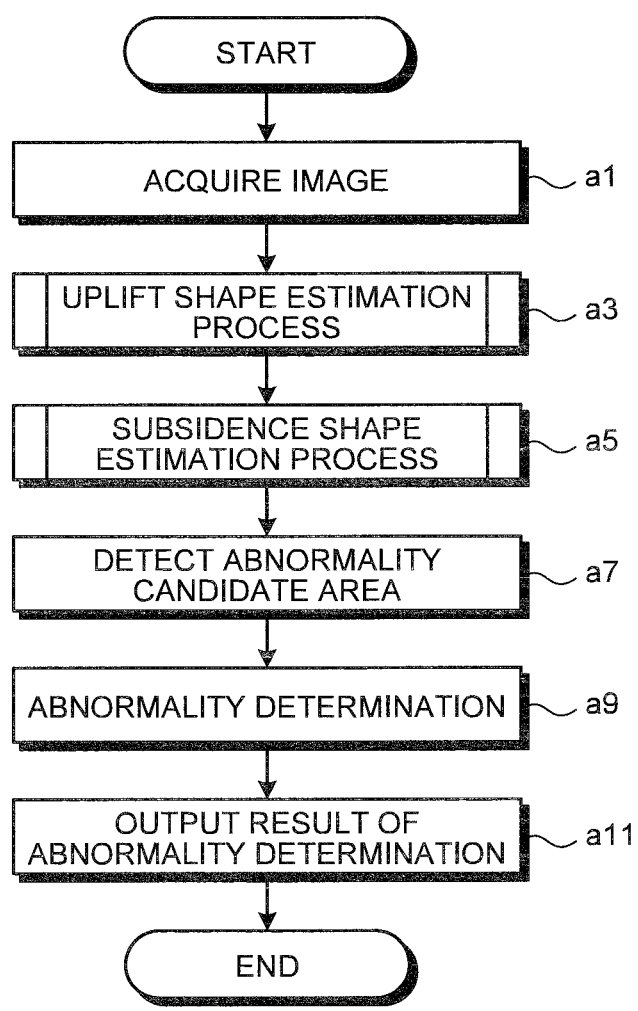
FIG. 3 is a flowchart illustrating a calculation process procedure that is performed by a calculating unit of the image processing apparatus.

FIG. 3 is a flowchart illustrating a calculation process procedure performed by the calculating unit 75 of the image processing apparatus 70. The process described here is performed by the calculating unit 75 by reading the image processing program 741 stored in the storage unit 74 and executing the image processing program 741.

Figure 4:
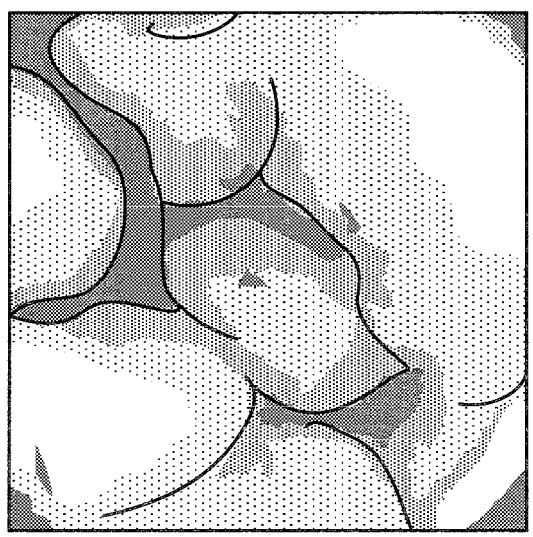
FIG. 4 is a view illustrating an example of a lumen in-vivo image.

As illustrated in FIG. 3, first, the calculating unit 75 acquires an image (lumen in-vivo image) via the external interface 71 and the controller 76 (step a1). FIG. 4 is a view illustrating an example of the image (lumen in-vivo image) that is acquired at step a1. The lumen in-vivo image that is captured by the capsule endoscope 3 shows the mucosa structure of the inner wall of the internal organ, which is an object, contents or bubbles that float in the lumen, and occasionally shows a crucial part such as a lesion. The mucosa structure of the inner wall of the internal organ includes uplift shapes and subsidence shapes because of folding and undulation of the internal organ or the mucosa of the inner wall.

Figure 5:
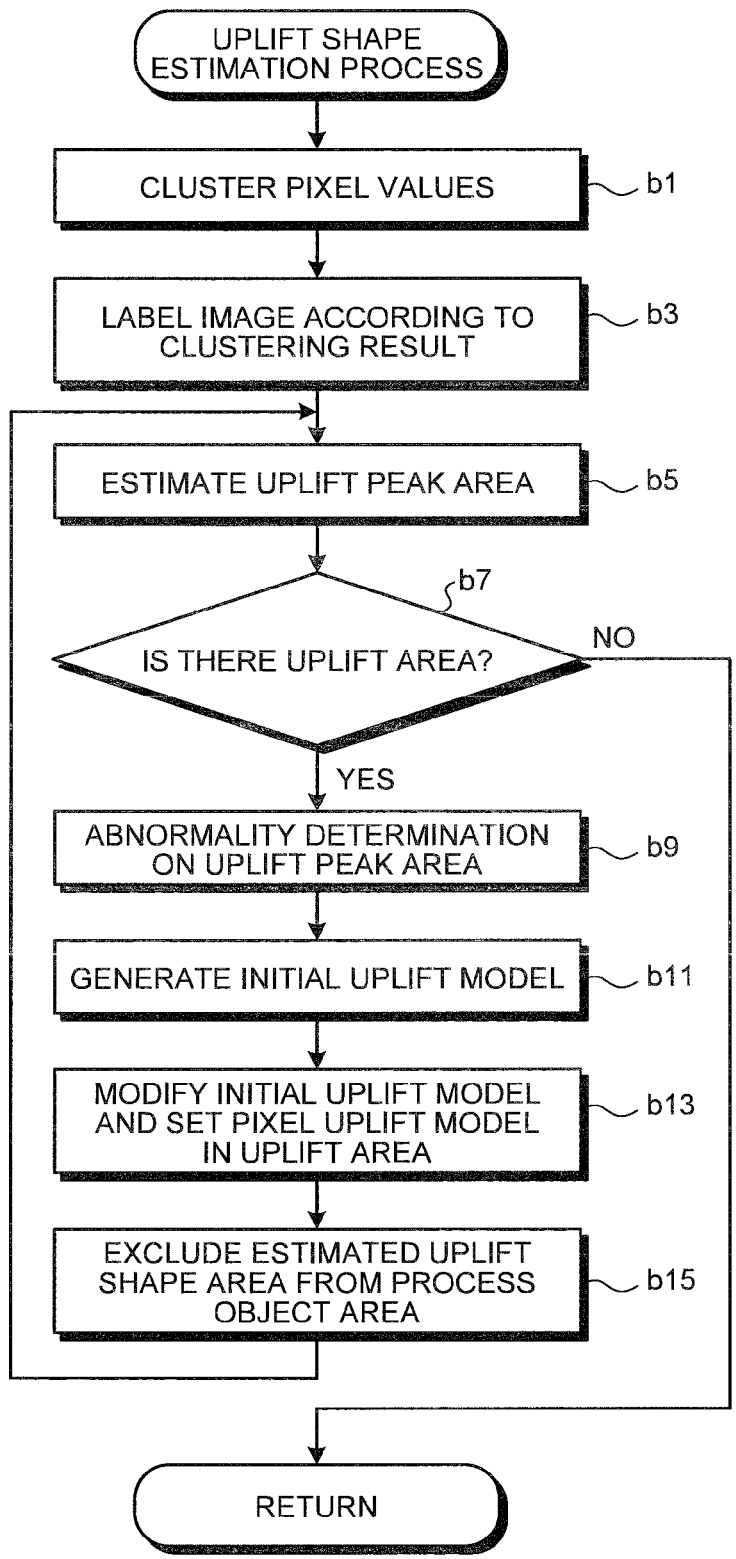
FIG. 5 is a flowchart illustrating a detailed process procedure of an uplift shape estimation process.

Subsequently, as illustrated in FIG. 3, the process proceeds to an uplift shape estimation process (step a3). FIG. 5 is a flowchart illustrating a detailed process procedure of the uplift shape estimation process.

In the uplift shape estimation process, first, the uplift peak estimator 751a serves as an area dividing unit and performs clustering on the pixels constituting the lumen in-vivo image according to the pixel values of R (red), G (green), and B (blue) (step b1). Well-known techniques may be used, such as clustering using the k-means method (see, p. 232, Digital image processing, CG-ARTS Association) or clustering by estimation of a mixture distribution using an EM algorithm (see, Maximum Likelihood from Incomplete Data via the EM Algorithm (A. P. Dempster, et al., Journal of the Royal Statistical Society. Service B (Methodological), Vol. 39, NO. 1. (1977), pp. 1-38)).

Figure 6:
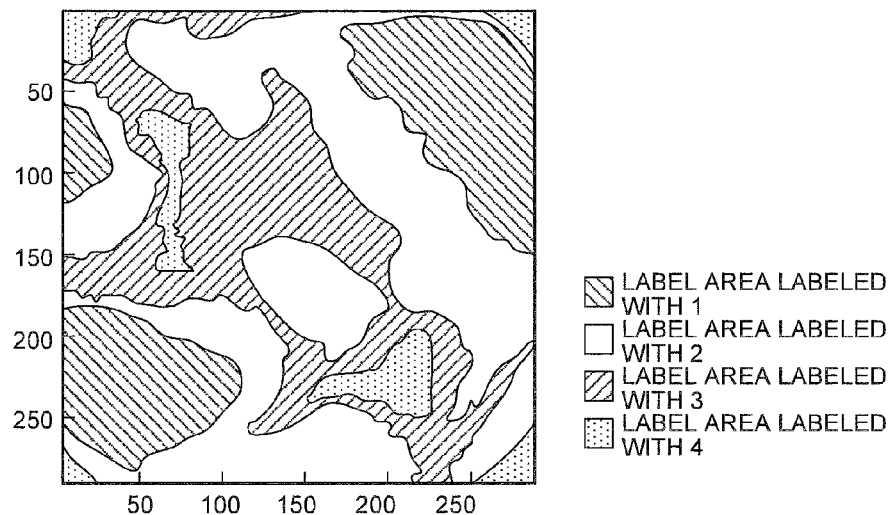
FIG. 6 is a view illustrating an example of a labeled image.

Subsequently, the uplift peak estimator 751a gives a label to each pixel of the acquired image according to the result of the clustering, thereby generating a labeled image (step b3). FIG. 6 is a view illustrating an example of a labeled image. For example, the uplift peak estimator 751a allocates labels (1, 2, 3 . . . ) in accordance with the luminance value of the center of gravity of each cluster in descending order of the luminance values. The uplift peak estimator 751a gives a label as a pixel value to each pixel, which is a label allocated to the cluster to which each pixel belongs. Accordingly, as illustrated in FIG. 6, a labeled image that is divided into label areas of the respective clusters is obtained. Label areas smaller than a pre-set certain area are excluded from the label areas subjected to the following processes. The areas to be processed in the following processes are referred to as a "process object area".

As illustrated in FIG. 5, the uplift peak estimator 751a then estimates uplift peak areas in the process object area according to the labeled image (step b5). Specifically, the uplift peak estimator 751a extracts, from label areas constituting the labeled image, a label area surrounded by a label area with a label larger than the label of its own label and sets the extracted label area as an uplift peak area.

Figure 7:
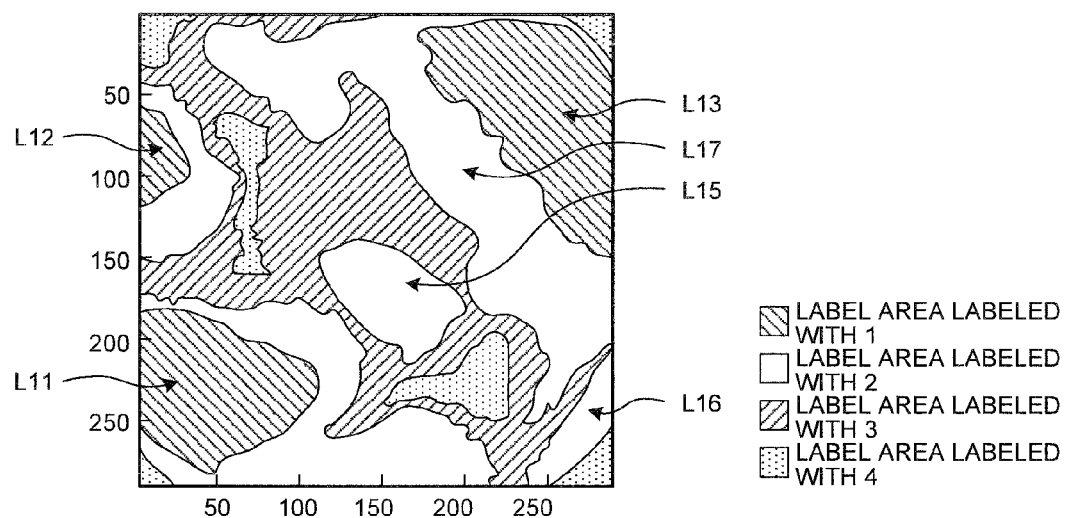
FIG. 7 is a view illustrating an uplift peak area that is estimated from the labeled image of FIG. 6.

FIG. 7 is a view illustrating uplift peak areas L11 to L13, L15, and L16 that are estimated from the labeled image of FIG. 6. As illustrated in FIG. 7, the label area L11 to L13, whose labels are "1" while neighboring labels are "2", and the label areas L15 and L16, whose labels are "2" while neighboring labels are "3" or "4", are extracted as uplift peak areas. Uplift peak areas are extracted in the ascending order of the labels, and label areas surrounding the label areas that are uplift peak areas are not extracted. For example, a label area L17 or the like whose label is "2" while its neighboring label is "3" is surrounded by a label area whose label is larger than the label of the label area L17. However, the label area L17 is not extracted because the label area L17 is the label area neighboring the label area L13 that is estimated as an uplift peak area. Note that estimation on whether the label area L17 is an uplift peak area is made later.

As illustrated in FIG. 5, when there is an uplift peak area that is estimated by the uplift peak estimator 751a (YES at step b7), the process proceeds to the processes at steps b9 to b13 in order to set a pixel uplift model in an uplift area in which the uplift peak area is the top portion. When there are plural estimated uplift peak areas, the processes at steps b9 to b13 are performed for each of the uplift peak areas.

At step b9, the uplift peak abnormality determining unit 753 performs an abnormality determination on the uplift peak areas and detects, as an abnormality candidate area, an uplift peak area that satisfies pre-set abnormality candidate conditions. In the abnormality determination on the uplift peak area, first, feature data of the uplift peak area is calculated. For example, tone information, such as an R value, a G value, and a B value of each pixel constituting the uplift peak area, the variation in tone between the uplift peak area and the area neighboring the uplift peak area, and the shape of the uplift peak area are calculated as feature data of the uplift peak area. Thereafter, the calculated feature data is compared with a prepared reference index so that an abnormality determination on the uplift peak area is made. For the reference index, for example, a range of feature data for each type of abnormality may be set as teaching data. In this case, the uplift peak abnormality determining unit 753 makes the abnormality determination using, as abnormality candidate conditions, a determination of whether the feature data of the uplift peak area is within the range of the feature data for each type of abnormality. Alternatively, normal samples may be prepared and the feature data of the uplift peak area may be calculated to set a range of feature data of the normal uplift peak area. In this case, the uplift peak abnormality determining unit 753 makes an abnormality determination using, as the abnormality candidate conditions, a determination of how much the feature data of the uplift peak area is outside of the range of feature data of the normal uplift peak area.

Figure 8:
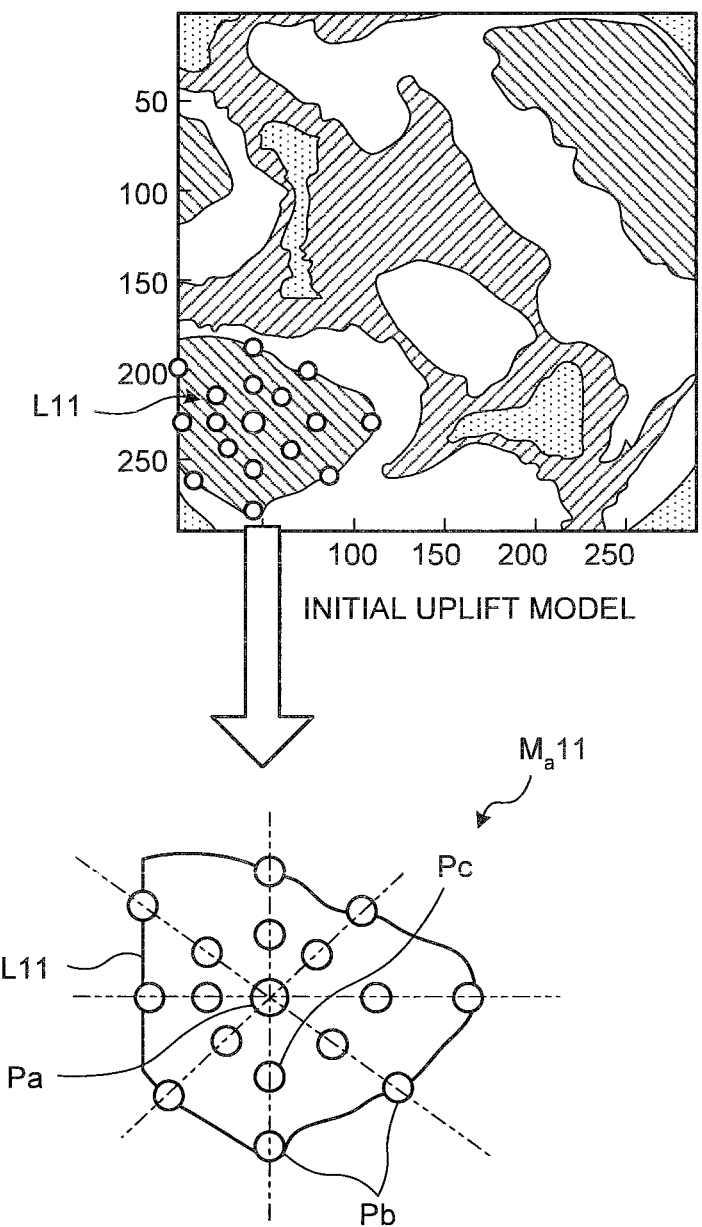
FIG. 8 is an explanatory view illustrating the principle of generating an initial uplift model.

According to the uplift peak area that is determined to be not abnormal, the pixel uplift model estimator 751b then generates an initial uplift model to be set in the uplift peak area (step b11). FIG. 8 is an explanatory view illustrating the principle of generating an initial uplift model and illustrating an initial uplift model $M_a11$ that is generated for the uplift peak area L11. When generating the initial uplift model $M_a11$, first, the center of gravity Pa of the uplift peak area L11 is calculated. The pixel uplift model estimator 751b, serving as a setting point arranging unit, performs a process in which points are set as edge points Pb at which the directions set radially from the calculated center of gravity Pa of the uplift peak area L11, as represented by the double-dashed lines in FIG. 8, intersect with the contour of the uplift peak area L11. The pixel uplift model estimator 751b then arranges middle points Pc between the center of gravity Pa and the edge points Pb. The positions at which the middle points are arranged are not limited to this. The middle points may be positioned at pre-set certain intervals. Also, the number of middle points is not necessarily be the same as the number of edge points. The number can be appropriately set.

Using the center of gravity, the edge points, and the middle points, an uplift area is modeled to generate the initial uplift model, which is an initial shape of a pixel uplift model. The peak (the highest point) of the uplift is close to the light source and the skirt of the uplift is distant from the light source; therefore, the pixel value (luminance) represented as the reflection of light from the light source increases the closer it is to the peak of the uplift and decreases the closer it is to the skirt. In this embodiment, this feature is used to model an uplift area, and an uplift shape is referred to as a "pixel uplift model". An uplift shape of such a "pixel uplift model" is three-dimensionally represented using the positions (x, y) for the center of gravity, the edge points, and the middle points and additionally using estimated pixel values (z) of the respective points. In other words, the estimated pixel values of the positions of the center of gravity, the edge points, and the middle points, which are calculated as described above, are obtained for the initial uplift model. When calculating the estimated pixel values of the positions of the center of gravity, the edge points, and the middle points, an edge is extracted of a proximate area covering pixels in positions proximate to each of the positions of the center of gravity, the edge points, and the middle points. Well-known methods can be properly employed as edge extraction methods. For example, edge detection using a Sobel filter may be performed (see, CG-ARTS Association, Digital image processing, pp. 116-P117). An average of pixel values of pixels in the proximate area excluding the pixels that are extracted as the edge in the edge extraction is calculated as an estimated pixel value of each position.

Subsequently, as illustrated in FIG. 5, the pixel uplift model modifier 751c modifies the pixel uplift model in the initial shape, which is the initial uplift model, and sets the modified pixel uplift model in the uplift area (step b13). The pixel uplift model (initial uplift model) is modified using an active contour model to move the edge points and the middle points.

Figure 9:
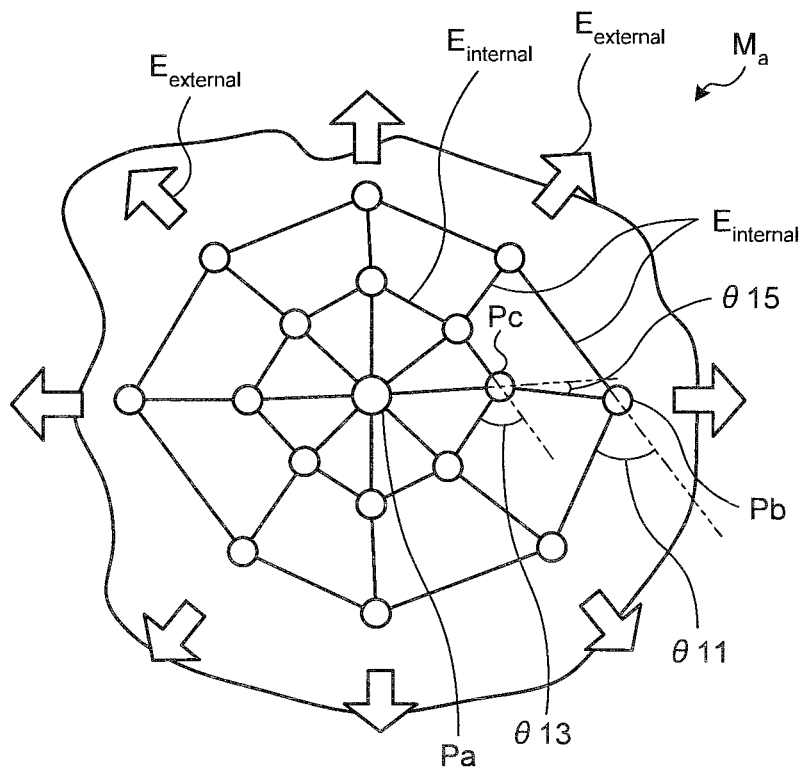
FIG. 9 is an explanatory view illustrating the principle of modifying a pixel uplift model.
Figure 10:
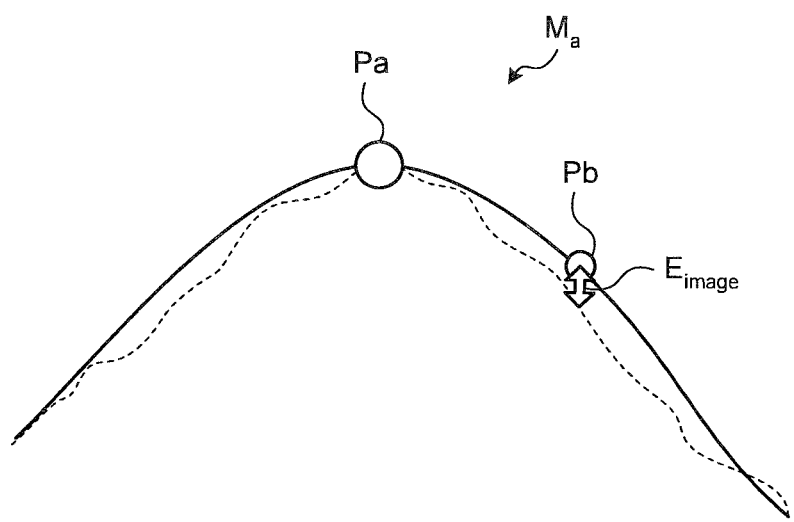
FIG. 10 is an explanatory view illustrating the principle of modifying the pixel uplift model.

FIGS. 9 and 10 are explanatory views illustrating the principle of modifying the pixel uplift model $M_a$. FIG. 10 illustrates a cross section of the pixel uplift model $M_a$ taken along the center of gravity Pa and an edge point Pb. The reference symbol $E_{internal}$ shown in FIG. 9 represents the energy representing continuousness and smoothness of lines connecting adjacent edge points Pb and middle points Pc. The energy $E_{internal}$ is defined as being small as the angle θ11 becomes small, which is an angle formed between the straight lines each connecting adjacent edge points Pb; as being small as the angle θ13 becomes small, which is an angle formed between the straight lines each connecting adjacent middle points Pc; or as being small as the angle θ15 becomes small, which is an angle formed between the straight line connecting a middle point Pc and the center of gravity Pa and the straight line connecting the middle point Pc and the edge point Pb adjacent to the middle point Pc. The reference symbol E external represents the energy that extends the pixel uplift model $M_a$ in accordance with the pixel gradient by moving the edge points Pb and the middle points Pc. The energy $E_{external}$ is defined as being small as the edge points Pb and the middle points Pc come away from the center of gravity Pa in accordance with the gradient of the actual pixel values. The reference symbol $E_{image}$ shown in FIG. 10 denotes compatibility energy of the edge points Pb with respect to the edge and denotes the pixel value difference energy between the estimated pixel values of the pixel uplift model $M_a$ and the actual pixel values that are represented by the dotted line shown in FIG. 10 in the uplift area in which the pixel uplift model $M_a$ is set. The energy $E_{image}$ is defined as being small as the edge points Pb are compatible with the edge that is detected using, for example, a Sobel filter and as the difference absolute value is small between the estimated pixel values of the edge points Pb and the middle points Pc and the actual pixel values in the positions of the edge points Pb and the middle points Pc.

Specifically, the energy $E_u$ of the active contour model is determined using the following Equation (1). In addition, the positions and estimated pixel values of the edge points and the middle points are obtained such that the value of the energy $E_u$ of the active contour model becomes the minimum. The reference symbols $\alpha_1, \alpha_2, \alpha_3$ denote predetermined coefficients.

$$E_u = \alpha_1 E_{internal} + \alpha_2 E_{external} + \alpha_3 E_{image} \quad (1)$$

Figure 11:
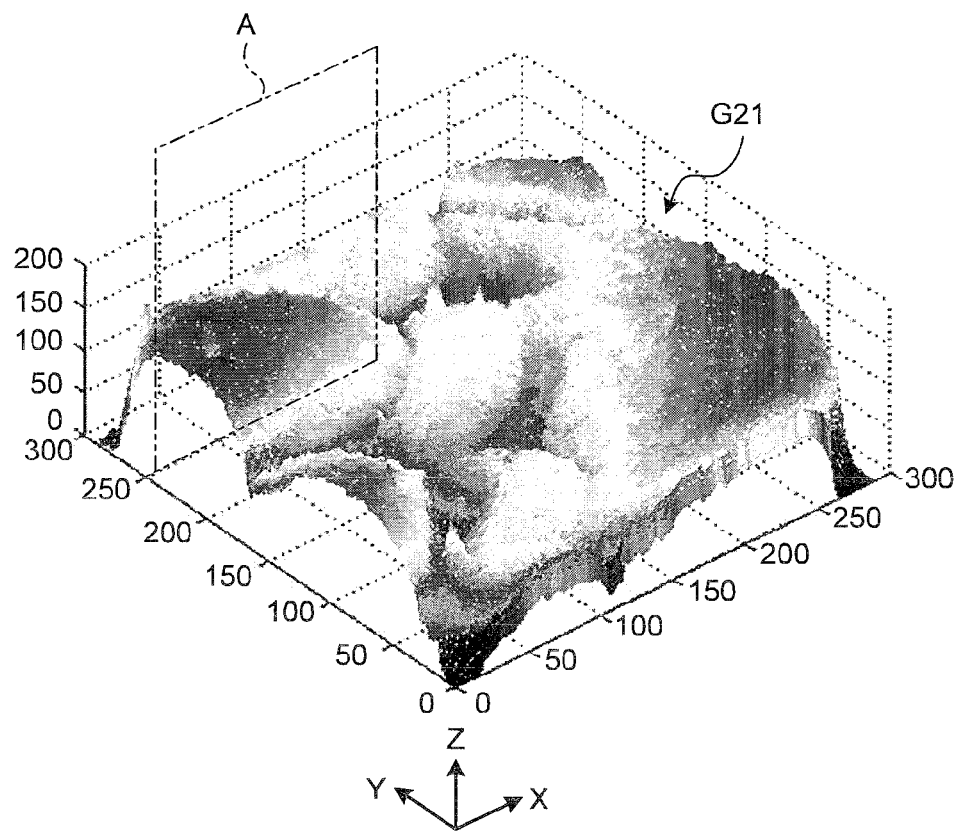
FIG. 11 is a view illustrating an example of a pixel value distribution of the lumen in-vivo image.
Figure 12:
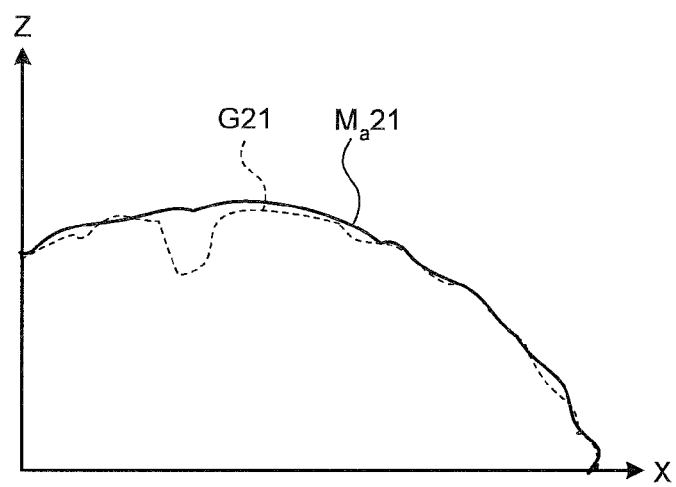
FIG. 12 is a cross-sectional view of a portion A of the pixel value distribution illustrated in FIG. 11.

FIG. 11 is a view illustrating an example of a pixel value distribution G21 of the lumen in-vivo image. FIG. 12 is a cross-sectional view of a portion A of the pixel value distribution in FIG. 11 illustrating the pixel value distribution G21 and a cross section of a pixel uplift model $M_a21$ that is set in the cross section of the portion A. Each pixel between the center of gravity and a middle point of the pixel uplift model and the pixel value (estimated pixel value) of each pixel between a middle point and an edge point are obtained by interpolation using linear interpolation or a spline curve interpolation.

The energy of attraction between adjacent edge points and middle points may be additionally defined and the pixel uplift model may be modified according to the energy. The method of extracting an uplift area is not limited to the above-described method. For example, a pixel uplift model in a predetermined distribution shape may be defined beforehand and the pixel uplift model may be modified presuming that an image is represented using an mixture distribution. In this case, the mixture distribution is estimated using an EM algorithm without extraction of an uplift peak area.

Figure 13:
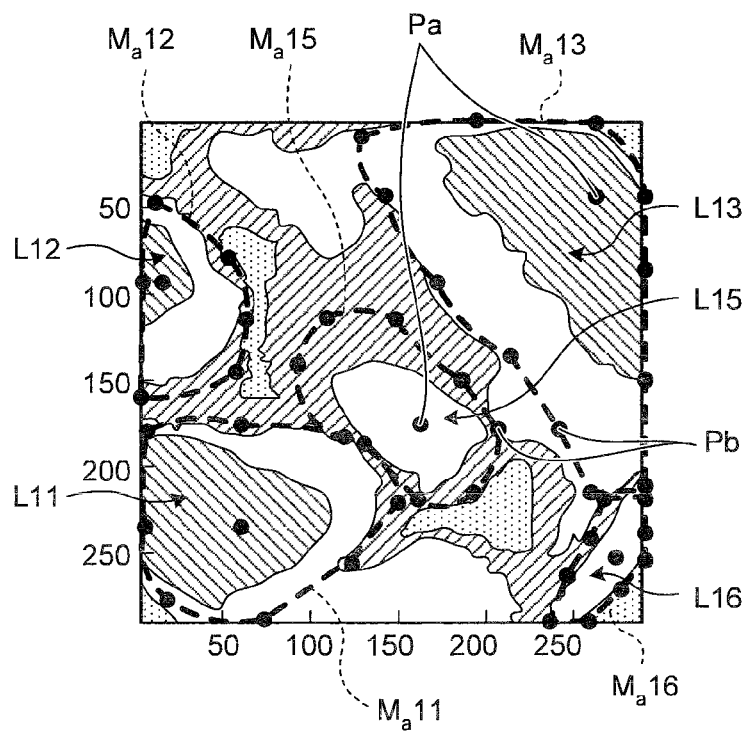
FIG. 13 is a view illustrating an image uplift model that is set according to the uplift peak area in FIG. 7.

FIG. 13 is a view illustrating pixel uplift models $M_a11$ to $M_a13$, $M_a15$, and $M_a16$ that are set according to the uplift peak areas L11 to L13, L15, and L16 that are represented in FIG. 7. FIG. 13 represents the outer shapes of the pixel uplift models $M_a11$ to $M_a13$, $M_a15$, and $M_a16$, which are represented by the dotted lines, and represents the centers of gravity Pa and the edge points Pb of the pixel uplift models. As a result of the processes at steps b9 to b13, as illustrated in FIG. 13, the pixel uplift models $M_a11$ to $M_a13$, $M_a15$, and $M_a16$ having uplift areas extended from the uplift peak areas L11 to L13, L15, and L16, respectively, are set in the image, and the uplift shapes in which the uplift peak areas L11 to L13, L15, and L16 serve as the top portions are estimated.

Back to FIG. 5, once the pixel uplift model modifier 751c has estimated the uplift shape and set the pixel uplift model as described above, the uplift area, for which the uplift shape is estimated and in which the pixel uplift models is set, is excluded from the process object area (step b15). The process then proceeds to step b5 and the uplift peak estimator 751a again estimates an uplift peak area according to the labeled image. When an uplift peak area is estimated (YES at step b7), a pixel uplift model is set (steps b9 to b13).

Figure 14:
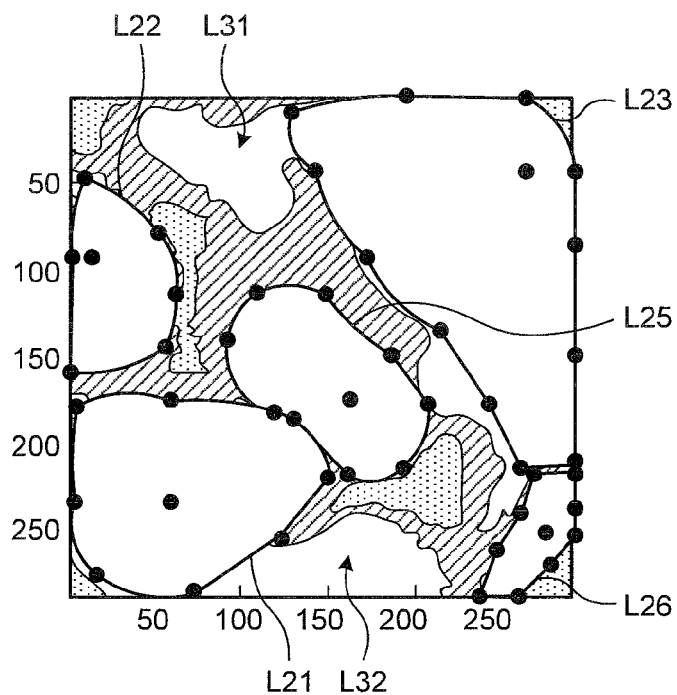
FIG. 14 is a view illustrating the uplift peak areas that is estimated excluding uplift areas.
Figure 15:
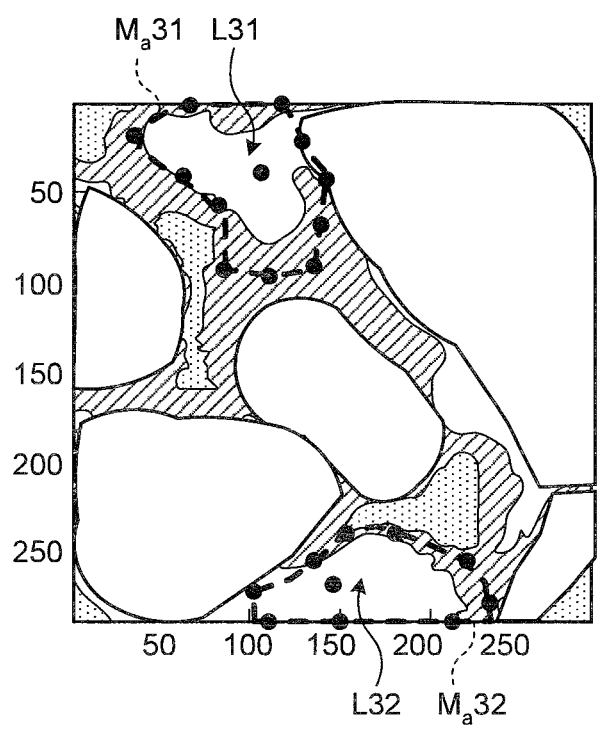
FIG. 15 is a view illustrating a pixel uplift model that is set according to the uplift peak areas in FIG. 14.

FIG. 14 is a view illustrating uplift peak areas L31 and L32 that are estimated and exclude the areas (uplift areas) L21 to L23, L25, and L26 in which the pixel uplift models are already set. FIG. 15 is a view illustrating pixel uplift models $M_a31$ and $M_a32$ that are set according to the uplift peak areas L31 and L32 illustrated in FIG. 14. In this process, as illustrated in FIG. 14, label areas that are surrounded by label numbers larger than those of the label areas are extracted as the uplift peak areas L31 and L32 from the process object area excluding the uplift areas L21 to L23, L25, and L26. In addition, as illustrated in FIG. 15, pixel uplift models $M_a31$ and $M_a32$ having uplift areas extended from the uplift peak area L31 and L32 are set in the image. As described above, the processes are repeated until no label area as an uplift peak area is extracted from the process object area. When no label area is extracted (NO at step b7), the process returns to step a3 and proceeds to step a5.

Figure 16:
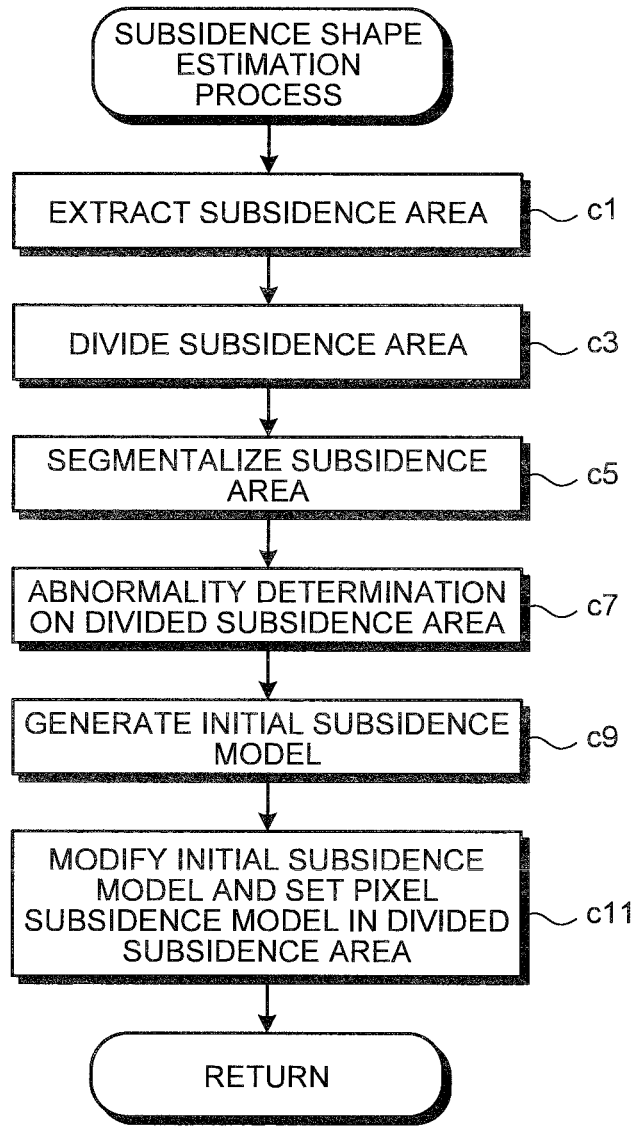
FIG. 16 is a chart illustrating a detailed process procedure of a subsidence shape estimation process.

At step a5, the process proceeds to a subsidence shape estimation process. FIG. 16 is a chart illustrating a detailed process procedure of the subsidence shape estimation process.

Figure 17:
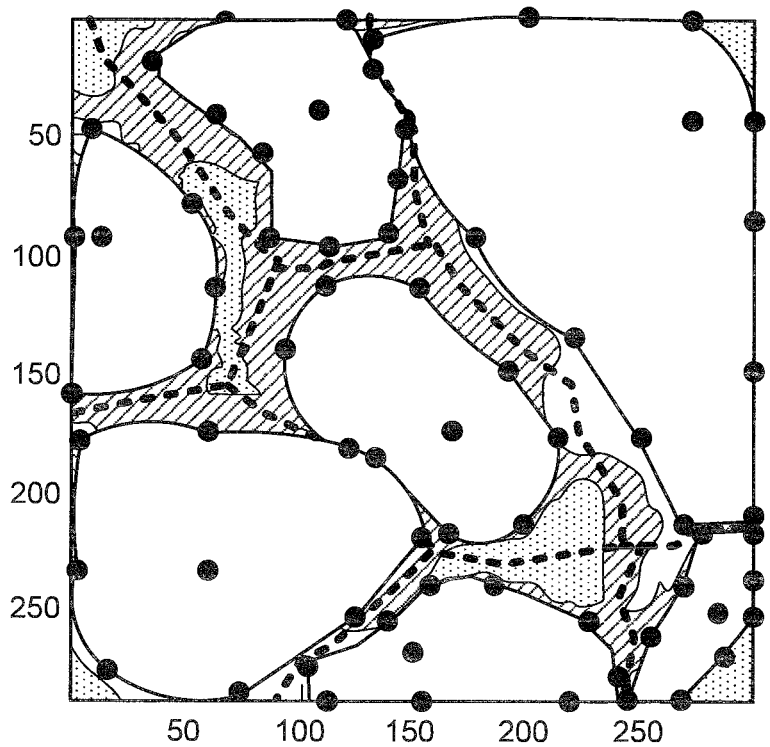
FIG. 17 is a view illustrating divided subsidence areas.

In the subsidence shape estimation process, first, the subsidence area extracting unit 752a extracts the area in the image, excluding the uplift areas, as a subsidence area between adjacent uplift areas (step c1). The subsidence area dividing unit 752b then divides the subsidence area (step c3). FIG. 17 is a view illustrating the divided subsidence areas. First, the subsidence area extracting unit 752a selects uplift areas most proximate to the pixels constituting the subsidence area. The subsidence area is then divided using, as dividing positions, the boundary positions that differentiate the selected uplift areas, as represented by the dotted lines in FIG. 17.

Subsequently, as illustrated in FIG. 16, the subsidence area dividing unit 752b further segmentalizes the divided subsidence areas (step c5). Specifically, the divided subsidence areas are segmentalized using the edge points of the pixel uplift models that are set in the uplift areas adjacent to the divided subsidence areas, i.e., uplift areas that are selected with respect to the pixels constituting the divided subsidence areas. For example, the divided subsidence areas may be segmentalized by dividing the divided subsidence areas at the positions of the edge points of the pixel uplift models in the subsidence gradient direction. The divided subsidence areas are not necessarily be divided at each position of the edge points. For example, they may be divided at, for example, every two edge points.

The divided subsidence area abnormality determining unit 754 then performs an abnormality determination on the segmentalized divided subsidence areas and detects, as an abnormality candidate area, a divided subsidence area that satisfies pre-set abnormality candidate conditions (step c7). The abnormality determination on the divided subsidence areas can be performed similarly to that of the abnormality determination performed by the uplift peak abnormality determining unit 753. In other words, first, feature data of a divided subsidence area is calculated. For example, tone information, such as an R value, a G value, and a B value of each pixel constituting the divided subsidence area, the variation in tone between the divided subsidence area and the area neighboring the divided subsidence area, and the shape of the divided subsidence area are calculated as feature data of the divided subsidence area. Thereafter, the calculated feature data is compared with a prepared reference index so that an abnormality determination on the divided subsidence area is made. When teaching data that determines a range of the feature data of each type of abnormality is prepared for the reference index, the divided subsidence area abnormality determining unit 754 makes an abnormality determination using, as the abnormality candidate conditions, a determination of whether the feature data of the divided subsidence area is within the range of the feature data of each type of abnormality. Alternatively, when normal samples are prepared and the feature data thereof is calculated to set a range of the feature data of the divided subsidence area, the divided subsidence area abnormality determining unit 754 makes an abnormality determination using, as the abnormality candidate conditions, a determination of how much the feature data of the divided subsidence area is outside of the range of the feature data of a normal divided subsidence area.

Figure 18:
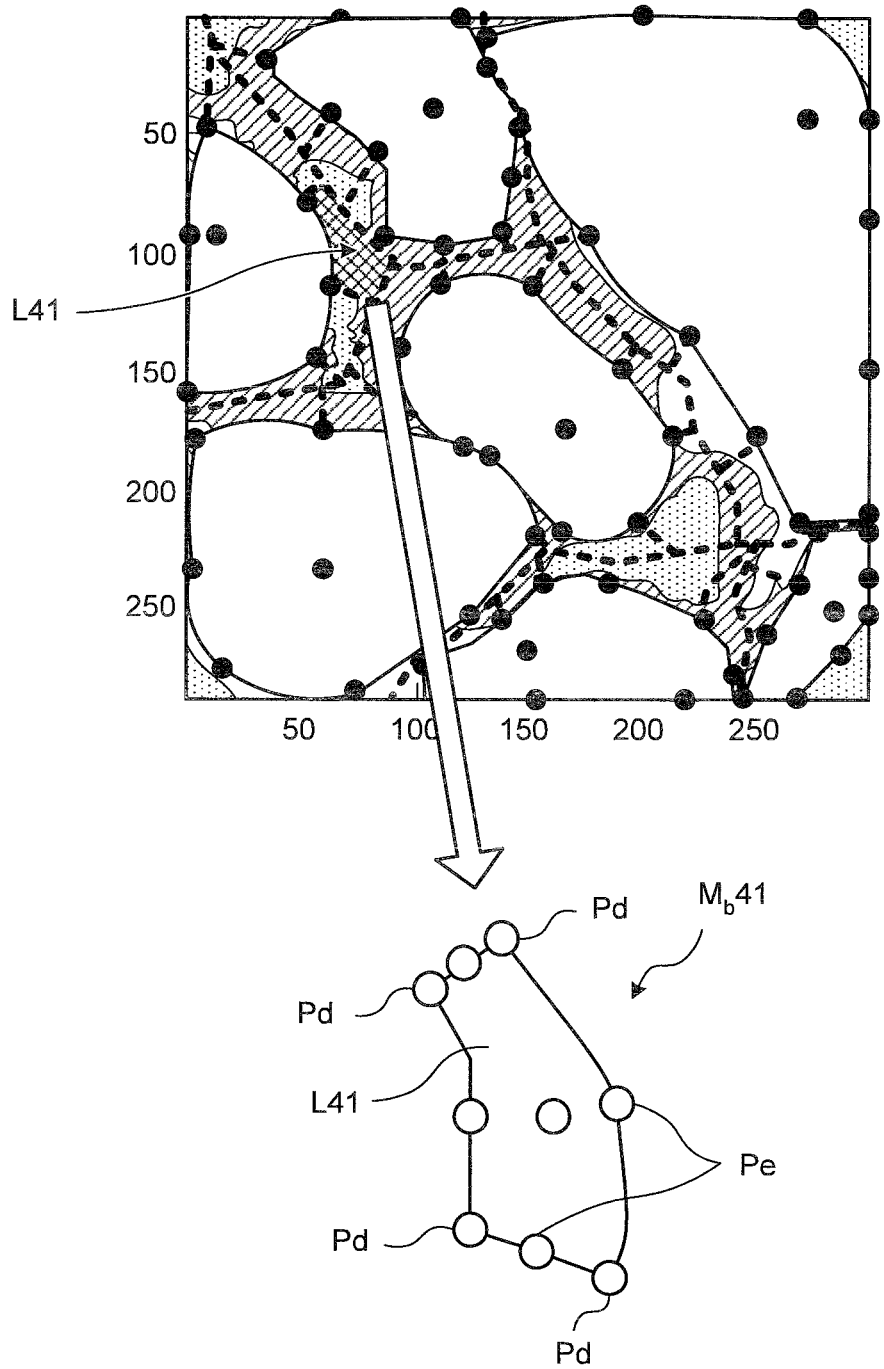
FIG. 18 is an explanatory view illustrating the principle of generating an initial subsidence model.

According to the divided subsidence area that is determined to be not abnormal, the pixel subsidence model estimator 752c then generates an initial subsidence model to be set in the divided subsidence area (step c9). FIG. 18 is an explanatory view illustrating the principle of generating an initial subsidence model and illustrating an initial subsidence model $M_b$41 that is generated for the segmentalized divided subsidence area L41. When generating the initial subsidence model $M_b$41, first, corners are set as edge points Pd according to the contour positions of the divided subsidence area L41. Middle points Pe are then arranged between the edge points Pd. For example, the middle points may be arranged at pre-set certain intervals or a pre-set certain number of middle points may be arranged. Using the edge points and the middle points, a subsidence area is modeled to generate the initial subsidence model, which is an initial shape of a pixel subsidence model. For estimated pixel values of the positions of the edge points and the middle points, like the generation of an initial uplift model, first, the edge of a proximate area covering pixels in positions proximate to each position is extracted. An average of the pixel values of the pixels in the proximate area excluding the pixels that are extracted as the edge in the edge extraction is calculated as an estimated pixel value of each position.

Subsequently, as illustrated in FIG. 16, the pixel subsidence model modifier 752d modifies the pixel subsidence model in the initial shape, which is the initial subsidence model, and sets the modified pixel subsidence model in the divided subsidence area (step c11). The pixel subsidence model (initial subsidence model) is modified by moving the edge points and the middle points using an active contour model.

Figure 19:
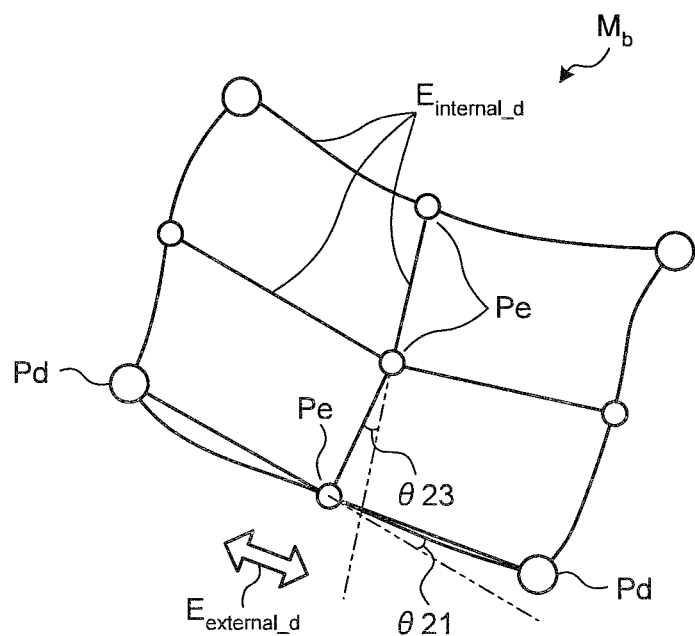
FIG. 19 is an explanatory view illustrating the principle of modifying a pixel subsidence model.
Figure 20:
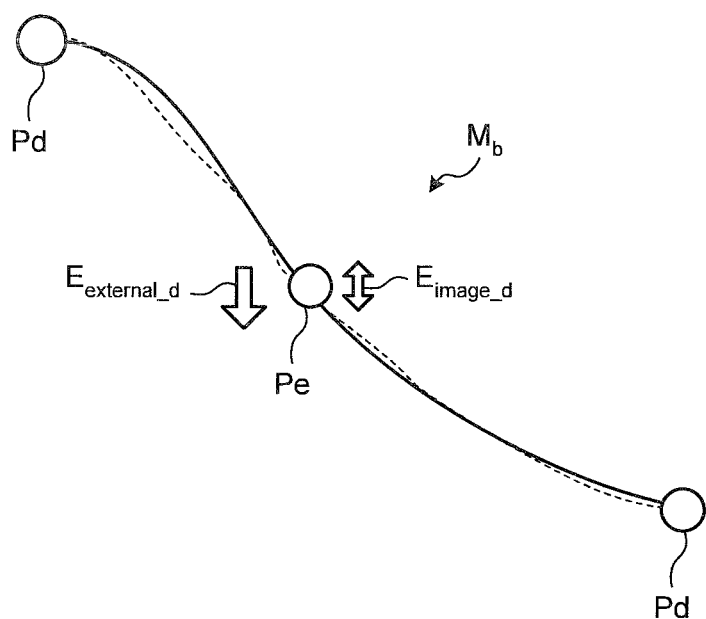
FIG. 20 is an explanatory view illustrating the principle of modifying the pixel subsidence model.

FIGS. 19 and 20 are explanatory views illustrating the principle of modifying the pixel subsidence model $M_b$. FIG. 20 illustrates a cross section of the pixel subsidence $M_b$ taken along an edge point Pd and a middle point Pe adjacent to the edge point Pd. The reference symbol $E_{internal\_d}$ shown in FIG. 19 represents the energy of continuousness and smoothness of the lines connecting adjacent edge points Pd and middle points Pe. The energy $E_{internal\_d}$ is defined as being small as the angle θ21 becomes small, which is an angle formed between the straight lines each connecting edge point Pb and middle point Pe that are adjacent to each other, and as the angle θ23 becomes small, which is an angle formed between the straight lines each connecting adjacent middle points Pe. The reference symbol $E_{external\_d}$ in FIGS. 19 and 20 represents the energy for moving the middle points Pe according to the pixel gradient. The energy $E_{external\_d}$ is defined as being small as the estimated pixel value of the middle point Pe in the pixel subsidence model (initial subsidence model) $M_b$ comes closer to the actual pixel value at the position of the middle point Pe. Alternatively, it is defined as being small as the position of the middle point Pe in the pixel subsidence model (initial subsidence model) $M_b$ moves toward a pixel, which is within a predetermined range of pixels including the position of the middle point Pe and at which variations relative to neighboring pixels are small. The reference symbol $E_{image\_d}$ shown in FIG. 20 denotes the pixel value difference energy between the estimated pixel values of the pixel subsidence model $M_b$ and the actual pixel values that are represented in the dotted line shown in FIG. 20 in the divided subsidence area in which the pixel subsidence model $M_b$ is set. The energy $E_{image\_d}$ is defined as being small as the difference absolute value becomes small between the estimated pixel values of the middle point Pe and the actual pixel values in the positions of the middle point Pe.

Specifically, the energy $E_d$ of the active contour model is determined using the following Equation (2). In addition, the positions and estimated pixel values of the edge points and the middle points are obtained such that the value of the energy $E_d$ of the active contour model becomes the minimum. The reference symbols $α_5, α_6, α_7$ denote predetermined coefficients.

$$E_d = α_5 E_{internal\_d} + α_6 E_{external\_d} + α_7 E_{image\_d} \quad (2)$$

Figure 21:
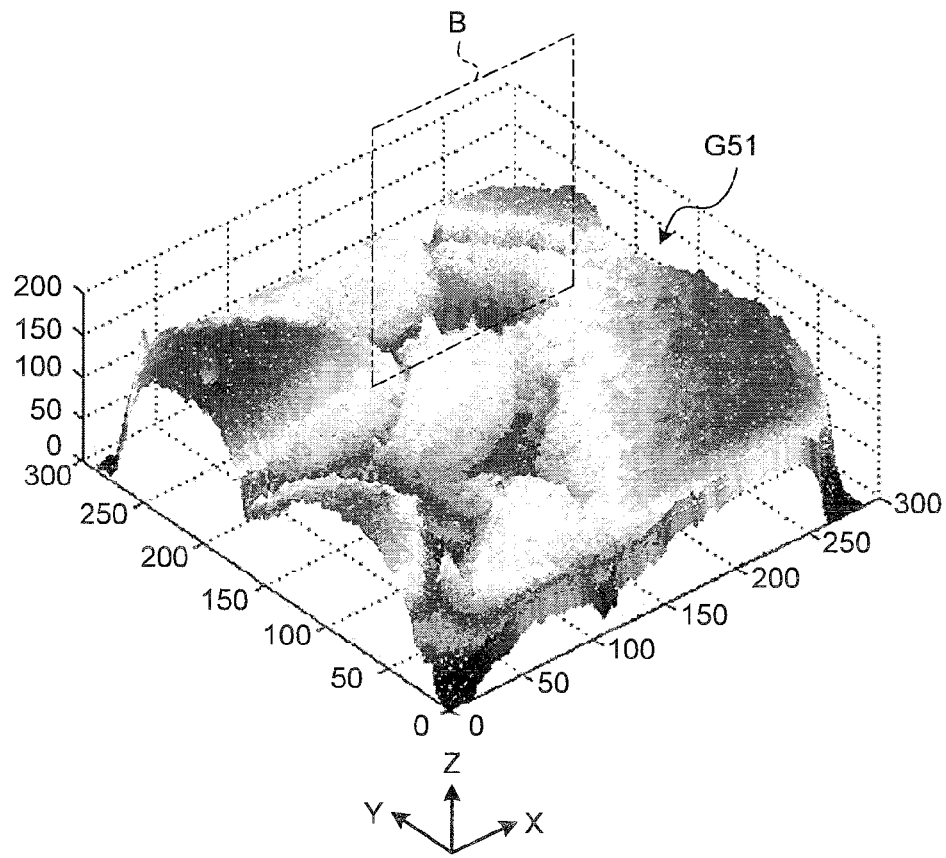
FIG. 21 is a view illustrating an example of a pixel value distribution of a lumen in-vivo image.
Figure 22:
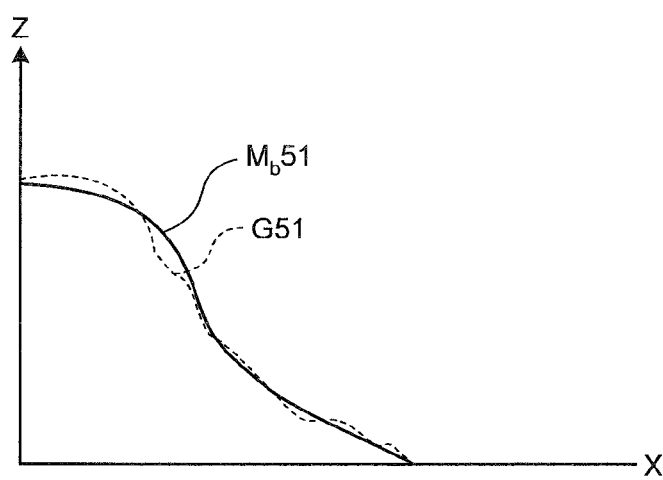
FIG. 22 is a cross-sectional view illustrating a portion B of the pixel value distribution in FIG. 21.

FIG. 21 is a view illustrating an example of the pixel value distribution G51 of the lumen in-vivo image. FIG. 22 is a cross-sectional view of a portion B of the pixel value distribution in FIG. 21, illustrating the pixel value distribution G51 in the cross section of the portion B and a cross section of a pixel subsidence model $M_b$51 that is set in the cross section of the portion B. The pixel value (modified pixel value) of each pixel between a middle point and an edge point in the pixel subsidence model is obtained by interpolation using linear interpolation or a spline curve interpolation. After this subsidence shape estimation process, the process returns to step a5 in FIG. 3 and then proceeds to step a7.

Figure 23:
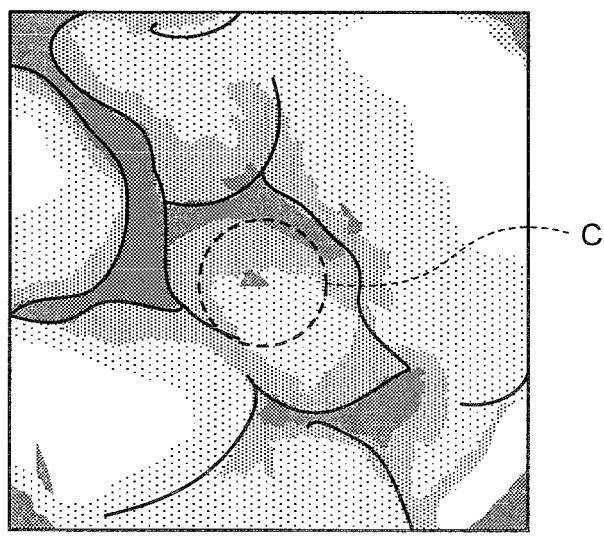
FIG. 23 is an explanatory view illustrating the principle of detecting an abnormality candidate area.
Figure 24:
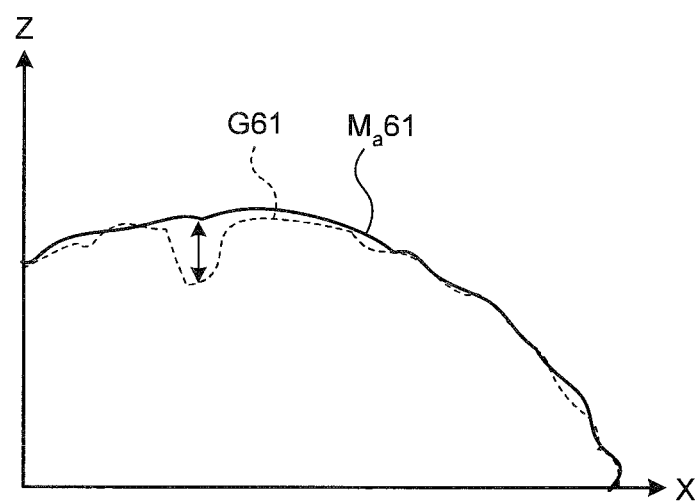
FIG. 24 is an explanatory view illustrating the principle of detecting an abnormality candidate area.
Figure 25:
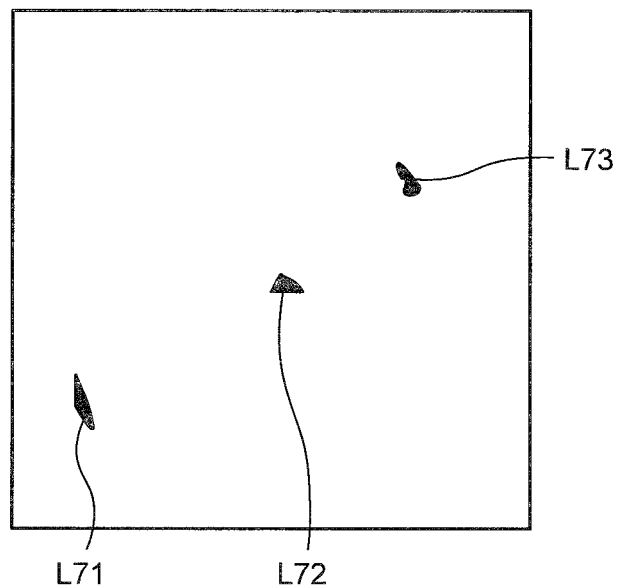
FIG. 25 is an explanatory view illustrating the principle of detecting an abnormality candidate area.

At step a7, the abnormality candidate detector 755 detects an abnormality candidate area. When detecting an abnormality candidate area, first, the abnormality candidate detector 755 compares the actual pixel value of each uplift area with that of the pixel uplift model. When the difference between the actual pixel value and the estimated pixel value of the pixel uplift model is equal to or more than a pre-set certain threshold that is set as an abnormality reference value range, the abnormality candidate detector 755 determines that the pixel value deviates from the pixel uplift model and detects the pixel value as a pixel constituting an abnormality candidate area. FIGS. 23 to 25 are explanatory views illustrating the principle of detecting an abnormality candidate area. FIG. 23 illustrates an example of the lumen in-vivo image. FIG. 24 shows a cross section of a pixel uplift model $M_a$61 that is set in an area C in the lumen in-vivo image shown in FIG. 23 and shows an actual pixel value distribution G61 in addition to the cross section of the pixel uplift model $M_a$61. In this process, like the pixel in the position represented by the arrow in FIG. 24, a pixel value whose actual pixel value is significantly different from the estimated pixel value in the pixel uplift model is detected as a pixel constituting an abnormality candidate area. Similarly, the actual pixel values of each divided subsidence area are compared with the pixel subsidence model. When the difference between an actual pixel value and an estimated pixel value of the pixel subsidence model is equal to or more than a certain threshold, which is pre-set as an abnormality reference value range, the pixel value is determined to deviate from the pixel subsidence model and is detected as a pixel constituting an abnormality candidate area. A well-known labeling process is then performed on the extracted pixels constituting the abnormality candidate areas and a unique label is added to connected pixels (see, CG-ARTS Association, Digital image process, pp. 181-182). As a result of labeling process, the abnormality candidate detector 755 detects areas to which the same label has been added as an abnormality candidate area. In the example of FIG. 25, three abnormality candidate areas L71 to L73 are detected.

Subsequently, the abnormality determining unit 756 makes an abnormality determination on the uplift peak areas that are detected as abnormality candidate areas at step b9 in FIG. 5, the divided subsidence areas that are detected as abnormality candidate areas at step c7 in FIG. 16, and the abnormality candidate areas that are detected at step a7 in FIG. 3. The abnormality determining unit 756 determines the abnormality candidate areas that satisfy the pre-set abnormal site conditions as areas that show abnormal sites of the object (step a9). In the abnormality determination, the tone information, such as an R value, a G value, and a B value of the abnormality candidate, the variation in tone between the abnormality candidate area and an area neighboring the abnormality candidate area, the edge intensity of the contour of the abnormality candidate area, and the shape of the abnormality candidate area are calculated as feature data of the abnormality candidate area. The abnormality determination on the abnormality candidate area is made by comparing the calculated feature data with a prepared reference index. When teaching data that determines the range of the feature data of each type of abnormality is prepared as a reference index, the abnormality determining unit 756 makes the abnormality determination using, as an abnormal site condition, a determination of whether the feature data of the abnormality candidate area is within the range of the feature data of each type of abnormality. Alternatively, when normal samples are prepared, the feature data of the abnormal candidate area is calculated, and the range of feature data of the normal abnormality candidate area is determined as a reference index, the abnormality determining unit 756 makes an abnormality determination using, as an abnormal site condition, a determination of how much the feature data of the abnormality candidate area is outside of the range of the feature data of the normal abnormality candidate area.

The calculating unit 75 outputs the result of the abnormality determination (step a11) and completes the calculation process. For example, the calculating unit 75 performs control for generating an image representing an uplift peak area, a divided subsidence area, or an abnormality candidate area that is determined to be abnormal and then outputting and displaying the positions on the image that are determined to be abnormal on the display unit 73 via the controller 76.

As described above, according to this embodiment, by setting, in an image, pixel uplift models obtained by modeling gradient variations in pixel values in an image, uplift shapes due to folding or undulation of a mucosa structure shown in the image can be estimated. In addition, by setting pixel subsidence models in the image, subsidence shapes of the mucosa structure shown in the image can be estimated. When an actual pixel value of an uplift area is compared with a corresponding pixel uplift model and if the difference between the actual pixel value and an estimated pixel value of the pixel uplift model is large and the pixel value deviates from the pixel uplift model, the pixel value is detected as a pixel constituting an abnormality candidate area. In addition, when an actual pixel value of a subsidence area is compared with a corresponding pixel subsidence model and if the difference between the actual pixel value and an estimated pixel value of the pixel subsidence model is large and the pixel value deviates from the pixel subsidence model, the pixel can be detected as a pixel constituting an abnormality candidate area. Abnormality candidate areas satisfying the pre-set abnormal site conditions, out of detected abnormality candidate areas, can be determined as areas that show abnormal sites of the mucosa structure. Accordingly, abnormality candidate areas that are shown in the mucosa structure in the lumen in-vivo image can be detected accurately without being influenced by variations in pixel values that appear in the image because of the shape of the mucosa structure.

In the above-described embodiment, the case is explained in which uplift shapes are estimated and then subsidence shapes are estimated. Alternatively, subsidence shapes may be estimated first. In such a case, pixel values in the image are clustered and a labeled image is generated by adding labels to the pixels according to the result of the clustering. Thereafter, subsidence bottom areas are estimated according to the labeled image. Specifically, a label area surrounded by a label area with a label smaller than the label of the label area (a label area with a luminance value smaller than the neighboring luminance value) is extracted as a subsidence bottom area. An initial subsidence model is generated according to the subsidence bottom area and the initial subsidence model is modified to set a pixel subsidence model. When estimating an uplift shape, a pixel uplift model is set in an area of the image excluding the subsidence area in which a pixel subsidence model is set.

According to the above-described embodiment, the case is described in which a lumen in-vivo image of the lumen that is captured by the capsule endoscope while moving through the body cavity is processed to detect an abnormality candidate area of the mucosa structure that is shown in the lumen in-vivo image. However, images that can be processed are not limited to lumen in-vivo images that are captured by the capsule endoscope. The detection is similarly applicable to the detection of an abnormal site of an object from an image of the object.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a model estimator that models gradient variations of pixel values in an image of a captured object, which is an in-vivo image, according to the pixel values in the image; and
   an abnormality candidate detector that detects an abnormality candidate area on the object shown in the image according to a difference between a pixel value of each pixel constituting the image and an estimated pixel value of each pixel, the estimated pixel value being determined according to the modeled gradient variations of the pixel values.

2. The image processing apparatus according to claim 1, wherein the model estimator models gradient variations of pixel values in an uplift area in the image and sets an uplift gradient model in the uplift area, the uplift area showing an uplift shape of the object.

3. The image processing apparatus according to claim 2, wherein the model estimator includes
   an initial uplift gradient model setting unit that sets an initial uplift gradient model of the uplift gradient model; and
   an uplift gradient model modifier that modifies the initial uplift gradient model based on the pixel values of pixels constituting an area of the image in which the initial uplift gradient model is set.

4. The image processing apparatus according to claim 3, further comprising an uplift peak estimator that detects a peak area of the uplift shape and estimates the peak area as a schematic position of the uplift area.

5. The image processing apparatus according to claim 4, wherein the initial uplift gradient model setting unit sets the initial uplift gradient model according to the peak area of the uplift shape.

6. The image processing apparatus according to claim 4, wherein
   the uplift peak estimator includes an area dividing unit that divides the image into areas according to the pixel values, and the uplift peak estimator compares pixel values of each of the areas, and detects, as the peak area, an area having pixel values higher than pixel values of a neighboring area.

7. The image processing apparatus according to claim 6, wherein the area dividing unit divides the image by clustering the pixel values in the image.

8. The image processing apparatus according to claim 7, wherein the area dividing unit clusters the pixel values using a k-means method.

9. The image processing apparatus according to claim 7, wherein the area dividing unit clusters the pixel values by estimating a distribution of the pixel values in the image by estimating a mixture distribution.

10. The image processing apparatus according to claim 3, wherein the uplift gradient model modifier deforms the uplift gradient model using an active contour model.

11. The image processing apparatus according to claim 4, further comprising an uplift peak abnormality determining unit that calculates feature data of the peak area and detects, as the abnormality candidate area, the peak area of which calculated feature data satisfies a predetermined abnormality candidate condition.

12. The image processing apparatus according to claim 2, wherein, according to a difference between the pixel value of each pixel constituting the uplift area and the estimated pixel value of each pixel constituting the uplift area, which is determined by the uplift gradient model set in the uplift area, the abnormality candidate detector detects a pixel, which has the difference in a predetermined abnormal reference value range, as a pixel constituting the abnormality candidate area.

13. The image processing apparatus according to claim 2, wherein the model estimator models gradient variations of pixel values in a subsidence area in the image and sets a subsidence gradient model in the subsidence area, the subsidence area showing a subsidence shape of the object.

14. The image processing apparatus according to claim 13, wherein the model estimator includes
an initial subsidence gradient model setting unit that sets an initial subsidence gradient model of the subsidence gradient model; and
a subsidence gradient model modifier that modifies the initial subsidence gradient model according to the pixel values of pixels constituting an area of the image in which the initial subsidence gradient model is set.

15. The image processing apparatus according to claim 13, further comprising a subsidence area extracting unit that extracts the subsidence area in the image.

16. The image processing apparatus according to claim 15, wherein the subsidence area extracting unit extracts, as the subsidence area, an area of the image excluding the uplift area in which the uplift gradient model is set.

17. The image processing apparatus according to claim 15, further comprising a subsidence area dividing unit that selects an uplift area most proximate to each pixel constituting the subsidence area and divides the subsidence area into areas having pixels corresponding to different ones of the selected uplift areas using boundaries as dividing positions.

18. The image processing apparatus according to claim 17, further comprising a setting point arranging unit that arranges a predetermined number of setting points or arranges setting points at predetermined intervals in contour positions of the uplift area,
wherein the subsidence area dividing unit further divides the divided subsidence areas using the setting points, which are set by the setting point arranging unit for the uplift area.

19. The image processing apparatus according to claim 14, wherein the subsidence gradient model modifier deforms the subsidence gradient model using an active contour model.

20. The image processing apparatus according to claim 15, further comprising a subsidence area abnormality determining unit that calculates feature data of each of the areas of the divided subsidence area and detects, as the abnormality candidate area, an area of which calculated feature data satisfies a predetermined abnormality candidate condition.

21. The image processing apparatus according to claim 1, further comprising an abnormality determining unit that calculates feature data of the abnormality candidate area and determines the abnormality candidate area, of which calculated feature data satisfies a predetermined abnormal site condition, to be an abnormal site of the object.

22. An image processing program recording device having stored thereon an image processing program that causes a computer to perform:
a model estimating procedure that models gradient variations of pixel values in an image of a captured object, which is an in-vivo image, according to the pixel values in the image; and
an abnormality candidate detecting procedure that detects an abnormality candidate area on the object shown in the image according to a difference between a pixel value of each pixel constituting the image and an estimated pixel value of each pixel, the estimated pixel value being determined according to the modeled gradient variations of the pixel values.

23. An image processing method comprising:
a model estimating step that models gradient variations of pixel values in an image of a captured object, which is an in-vivo image, according to the pixel values in the image; and
an abnormality candidate detecting step that detects an abnormality candidate area on the object shown in the image according to a difference between a pixel value of each pixel constituting the image and an estimated pixel value of each pixel, the estimated pixel value being determined according to the modeled gradient variations of the pixel values.

* * * * *